(12) United States Patent
Grisenti et al.

(10) Patent No.: US 7,727,751 B2
(45) Date of Patent: Jun. 1, 2010

(54) METHOD FOR THE PREPARATION OF MYCOPHENOLATE MOFETIL BY ENZYME TRANESTERIFICATION

(75) Inventors: Paride Grisenti, Milan (IT); Paolo Prestileo, Milan (IT)

(73) Assignee: Poli Industria Chimica SpA, Milan (IT)

( * ) Notice: Subject to any disclaimer, the term of this patent is extended or adjusted under 35 U.S.C. 154(b) by 604 days.

(21) Appl. No.: 11/661,913

(22) PCT Filed: Jul. 25, 2005

(86) PCT No.: PCT/EP2005/053629

§ 371 (c)(1),
(2), (4) Date: Mar. 2, 2007

(87) PCT Pub. No.: WO2006/024582

PCT Pub. Date: Mar. 9, 2006

(65) Prior Publication Data

US 2008/0085542 A1    Apr. 10, 2008

(30) Foreign Application Priority Data

Sep. 3, 2004    (IT) .......................... MI2004A1703

(51) Int. Cl.
*C12P 7/62* (2006.01)
(52) U.S. Cl. .......................... 435/135; 435/41; 435/132; 435/171; 435/198

(58) Field of Classification Search ........................ None
See application file for complete search history.

(56) References Cited

U.S. PATENT DOCUMENTS

2004/0167130 A1    8/2004    Lee et al.

FOREIGN PATENT DOCUMENTS

WO    WO03/042393    5/2003

OTHER PUBLICATIONS

Santaniello Enzo, et al., "Lipase-catalyzed transesterification in organic solvents: applications to the preparation of enantiomerically pure compounds" Enzyme and Microbial Technology, vol. 15, No. 5, p. 367-382, 1993.
International Search Report and the Written Opinion for PCT/EP2005/053629 of Nov. 7, 2005.

*Primary Examiner*—L Blaine Lankford
*Assistant Examiner*—Kade Ariani
(74) *Attorney, Agent, or Firm*—Hueschen and Sage

(57) ABSTRACT

The present invention relates to a process for the preparation of mycophenolate mofetil (MMF) in which an ester of mycophenolic acid (MPA) with a low-molecular-weight aliphatic alcohol is transesterified with N-(2-hydroxyethyl)morpholine in the presence of *Candida antarctica* lipase, and in which the MPA esterification reaction is carried out in the presence of *Candida antarctica* lipase using the corresponding alcohol as the solvent.

24 Claims, No Drawings

METHOD FOR THE PREPARATION OF MYCOPHENOLATE MOFETIL BY ENZYME TRANESTERIFICATION

Mycophenolate mofetil (MMF; Registry Number 128794-94-5), the ester of mycophenolic acid (MPA; Registry Number 24280-93-1) with N-(2-hydroxyethyl)morpholine (Registry Number 622-40-2), is an immunosuppressant currently used in the treatment of patients who have undergone a kidney transplant.

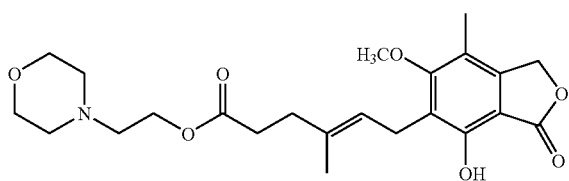

after oral administration, MMF is hydrolyzed with MPA, which is the real immunosuppressant agent, because it is a powerful inhibitor of inosine monophosphate dehydrogenase (B. J. Bornes, A. E. Eakin, R. A. Izydore and I. H. Hall Biochemical Pharmacology, 62, (2001), p. 91-100).

MMF was described for the first time in U.S. Pat. No. 4,753,935 (1987, to which the patent EP 028713B1 corresponds): in that patent, the preparation of MMF is described by conventional methods of esterification of MPA with N-(2-hydroxyethyl)morpholine. Those methods provide for condensation between the MPA and the N-(2-hydroxyethyl)morpholine by means of the acyl chloride of MPA or by using a condensing agent, such as, for example, dicyclohexylcarbodiimide. Those synthesis methods have, however, the disadvantage of leading, apart from to the desired product, to a series of secondary MPA polycondensation products owing to the simultaneous presence on the molecule of a phenolic hydroxyl and of a lactone function in addition to the carboxylic group.

In order to overcome that problem, alternative methods of preparing MMF have recently been developed. Some methods, described in the patent applications WO 00-34503 (2000) and WO 03-042393 (2003), report on the preparation of MMF using a biocatalytic method, by reaction between MPA and N-(2-hydroxyethyl)morpholine by enzymatic catalysis. For it is known that many hydrolytic enzymes, such as, for example, lipases, esterases or proteases, which are nowadays readily commercially available, used in organic solvents and with rigorous control of the experimental conditions (the water content, pH, temperature, presence of surfactants and water scavengers) are capable not only of performing the hydrolysis of non-natural substrates but also of catalyzing the synthesis of esters (Klibanov A. M. CHEMTECH, 1986, 16, 354; Schopineau J., McCafferty F. D., Therisod M., Klibanov A. M. Biotechnol. and Bioeng. 1988, 31, 208; Therisod M., Klibanov A. M. Journal of Chemical American Society, 1987, 109, 3977).

Nor are those enzymatic methods entirely satisfactory, however, because the presence of water, which is produced during the esterification reaction or contained in the reaction medium, has a considerable influence on the level of progress of the reaction, while the use of a surfactant in the reaction medium may complicate the subsequent procedures of purifying the MMF from the crude reaction product. In addition, the type of organic solvent used may have a strong influence on the reaction kinetics and the catalytic efficiency of the enzyme, leading in some cases to long reaction times in order to obtain a level of progress of the reaction acceptable for the application thereof in key industrial preparations.

We therefore decided to establish whether it was not possible to find suitable experimental conditions which would enable us to carry out the preparation of MMF, through the use of enzymes, by operating in the absence of surfactants and without rigorous control of the pH conditions and of the presence of water in the reaction medium. Because the literature describes numerous examples of the application in organic chemistry of enzymatic transesterification reactions catalyzed by lipases, we decided to establish whether this approach could be applied successfully also to the preparation of MMF (E. Santaniello, P. Ferraboschi and P. Grisenti. Enzyme Microb. Technol. 1993, vol 15, p. 367-382). In order to do that, it would have been necessary to identify the most suitable hydrolytic enzyme for carrying out both the MPA esterification reaction with a simple alcohol, and the subsequent transesterification with N-(2-hydroxyethyl)morpholine. By studying various reaction conditions for the enzymatic esterification of MPA with various aliphatic alcohols and by using as the enzymatic catalyst various lipases (triacyl glycerol lipases, EC 3.1.1.3) we surprisingly established that the esterification, catalyzed by Candida antarctica lipase (CAL B, Novozym 435), of MPA with low-molecular-weight aliphatic alcohols, such as, for example, ethanol or methanol, leads quantitatively to the corresponding ethyl or methyl esters in from 30 to 40 hours. This method, which uses the same aliphatic alcohol (i.e. methanol or ethanol) as the only reaction solvent, is not affected significantly by the formation of water which is generated in the reaction environment and does not require the use of a surfactant.

In addition, CAL B under the experimental conditions we used, but employing as the reaction solvent isopropanol, 2,2,2-trifluoroethanol, 2,2,2-trichloroethanol, n-propanol and n-butanol, enabled us to obtain, analogously to the use of methanol and ethanol, the corresponding MPA esters.

The subsequent transesterification reaction of these MPA esters with N-(2-hydroxyethyl)morpholine in tetrahydrofuran (THF), still catalyzed by CAL B, proved capable of leading quantitatively to MMF without providing for the use of a surfactant and in an anhydrous environment (FIG. 1).

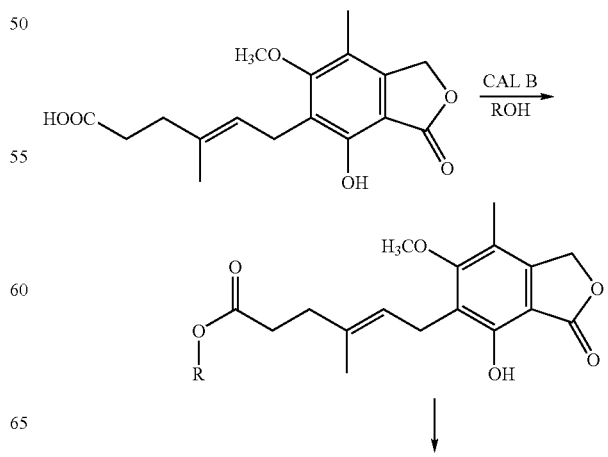

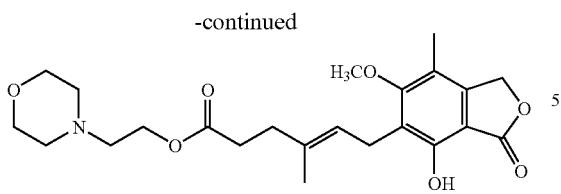

1. R = CH₃—
2. R = CH₃CH₂—
3. R = CH₃CH₂CH₂—
4. R = (CH₃)₂CH—
5. R = CF₃CH₂—
6. R = CCl₃CH₂—
7. R = CH₃(CH₂)₃—

The specificity between MPA and CAL B was all the more surprising if it is borne in mind that, under the same experimental conditions, other lipases, such as *Pseudomonas cepacia* lipase (PCL) or *Candida rugosa* lipase (CRL), did not show themselves capable of leading to the corresponding methyl or ethyl esters or of catalyzing transesterification reactions with N-(2-hydroxyethyl)morpholine.

Those lipases, which are known in the literature for being capable of catalyzing esterification and transesterification reactions on various non-natural substrates, are apparently not capable, under the experimental conditions we used, of accepting MPA in their active site.

The MPA esterification reaction is carried out in a typical manner using CAL B as the enzyme and the appropriate alcohol as the solvent, preferably a $C_1$-$C_4$ alkyl alcohol or a halogenated derivative thereof. The preferred amount of enzyme used is from 20 to 60 mg per mmole of MPA, preferably 53 mg. The concentration of MPA is from 0.05 to 0.2 molar, preferably 0.1 molar. The reaction is carried out under agitation at a temperature of from 15 to 45° C., preferably 30° C. for a period of time of from 30 to 40 hours. The reaction is completed by removing the enzyme by filtration and concentrating the filtrate under vacuum.

The transesterification reaction of the MPA esters with N-(2-hydroxyethyl)morpholine is carried out in a typical manner using CAL B as the enzyme and an aprotic polar organic solvent, preferably having a log P of less than 0.5, and even more preferably THF or 1,4-dioxan.

The preferred amount of enzyme used is from 50 to 150 mg per mmole of substrate, preferably 107 mg. The concentration of the substrate is from 0.1 to 0.3 molar, preferably 0.25. The molar ratio between the MPA ester and the N-(2-hydroxyethyl)morpholine is from 0.2 to 0.4, preferably 0.3. The reaction is carried out under agitation at a temperature of from 15 to 45° C., preferably at from 25 to 30° C. for a period of time of from 24 to 36 hours and is then completed by removing the enzyme by filtration and concentrating the filtrate under vacuum. Alternatively, the MPA esterification reaction and the subsequent transesterification reaction with N-(2-hydroxyethyl)morpholine can be carried out by re-using the same enzyme without any apparent loss of enzyme activity compared with the use of a "fresh" enzyme.

In addition, CAL B under the experimental conditions described above can be used in more use cycles, both in esterification and in transesterification, without any appreciable loss of catalytic activity.

EXPERIMENTAL PART

Example 1

Preparation of Mycophenolic Acid Ethyl Ester (2)

1.01 g (3.15 mmoles) of MPA are dissolved under agitation at a temperature of 30° C. in 37.5 ml of absolute ethanol, and then 170 mg of CAL B are added. The reaction mixture is maintained under vigorous agitation for 40 hours at the temperature of 30° C. and then the reaction is completed: the enzyme is removed by filtration and the filtered solution is concentrated under vacuum to give an oily residue. The oily residue is taken up with dichloromethane (20 ml) and the organic solution obtained is washed in sequence with a saturated sodium bicarbonate solution (15 ml) and then with water. The organic phase is then dried over sodium sulphate, filtered and concentrated under vacuum to give 1.042 g (2.99 mmoles; 95% yield) of mycophenolic acid ethyl ester (2) which is used directly in the next synthesis step without any further purification.

Elemental analysis calculated for $C_{19}H_{24}O_6$: C=65.50; H=6.94; O=27.55. Found: C=65.42; H=6.90; O=27.44.

Mass spectrum (analytical fragments): 349 (m+1), 348 (molecular ion), 303 (m−45)

$^1$H-NMR (500 MHz) CDCl₃: 1.16 (t, 3H, C$\underline{H}_3$—CH₂—), 1.76 (s, 3H, CH₃—C=), 2.15 (s, 3H, CH₃—Ar), 2.26 (m, 2H, CH₂—C=), 2.35 (m, 2H, CH₂CO), 3.35 (d, 2H, CH₂Ar), 3.75 (s, 3H, OCH₃), 4.04 (q, 2H, CH₃—C$\underline{H}_2$O), 5.16 (s, 2H, ArCH₂O), 5.20 (t, 1H, CH=).

The following MPA esters were also prepared in an analogous manner: methyl ester, 2,2,2-trifluoroethyl ester, 2,2,2-trichloroethyl ester, propyl ester, i-propyl ester, n-butyl ester.

Methyl Ester (1)

Elemental analysis calculated for $C_{18}H_{22}O_6$: C=64.66; H=6.63; O=28.71. Found: C=64.59; H=6.54; O=28.65

Mass spectrum (analytical fragments): 335 (m+1), 334 (molecular ion), 303 (m−31)

n-propyl Ester (3)

Elemental analysis calculated for $C_{20}H_{26}O_6$: C=66.28; H=7.23; O=26.49. Found: C=66.18; H=7.15; O=26.37

Mass spectrum (analytical fragments): 363 (m+1), 362 (molecular ion), 319 (m−43)

Isopropyl Ester (4)

Elemental analysis calculated for $C_{20}H_{26}O_6$: C=66.28; H=7.23; O=26.49. Found: C=66.20; H=7.17; O=26.40.

Mass spectrum (analytical fragments): 363 (m+1), 362 (molecular ion), 319 (m−43)

2,2,2-trifluoroethyl Ester (5)

Elemental analysis calculated for $C_{19}H_{21}F_3O_6$: C=56.72; H=5.26; F=14.17; O=23.86. Found: C=56.63; H=5.18; F=14.11; O=23.80.

Mass spectrum (analytical fragments): 403 (m+1), 402 (molecular ion), 303 (m−99)

2,2,2-trichloroethyl Ester (6)

Elemental analysis calculated for $C_{19}H_{21}Cl_3O_6$: C=50.52; H=4.69; Cl=23.54; O=21.25. Found: C=50.43; H=4.65; Cl=23.45; O=21.14.

Mass spectrum (analytical fragments): 458 (m+6), 456 (m+4), 454 (m+2), 452 (molecular ion), 303 (m−149)

n-butyl Ester (7)

Elemental analysis calculated for $C_{21}H_{28}O_6$: C=67.00; H=7.50; O=25.50. Found: C=66.92; H=7.42; O=25.40.

Mass spectrum (analytical fragments): 377 (m+1), 376 (molecular ion), 303 (m−73)

Example 2

Preparation of MMF by Transesterification of Mycophenolic Acid Ethyl Ester 195 mg (0.56 mmole) of mycophenolic acid ethyl ester are dissolved, under agitation at a temperature of from 25 to 30° C., in anhydrous THF (2 ml). 60 mg of CAL B and 0.23 ml (249 mg, 1.9 mmoles) of N-(2-hydroxyethyl)morpholine are then added. The reaction mixture is maintained under agitation at the temperature of from 25 to 30° C. for 35 hours. After this period, the reaction is completed: the enzyme is removed by filtration and the filtered solution is concentrated under vacuum to give an oily residue. The oily residue is taken up with dichloromethane (20 ml) and the organic solution obtained is washed in sequence with a saturated sodium bicarbonate solution (15 ml) and then with water. The organic phase is then dried over sodium sulphate, filtered and concentrated under vacuum to give 206 mg (0.45 mmole; 82% yield) of MMF. For analytical purposes, this product was purified by chromatography over silica gel (1/100=p/p): by elution with dichloromethane/methanol=96/4 v/v, 143 mg of purified MMF are recovered.

$^1$H-NMR (500 MHz) $CDCl_3$: 1.80 (s, 3H, $CH_3$—C=), 2.18 (s, 3H, $CH_3$—Ar), 2.20-2.45 (m, 4H, $CH_2$—N and $CH_2$—C=), 2.48 (m, 4H, 2 $CH_2$—N), 2.60 (m, 2H, $CH_2CO$), 3.40 (d, 2H, $CH_2Ar$), 3.78 (m, 4H, $CH_2O$), 3.80 (s, 3H, $OCH_3$), 4.20 (t, 2H, $CH_2O$), 5.15-5.30 (m, 3H, $CH_2O$ and CH=).

MMF was prepared in an analogous manner by transesterification also starting from the following MPA esters: methyl ester, 2,2,2-trifluoroethyl ester, 2,2,2-trichloroethyl ester, n-propyl ester, i-propyl ester, n-butyl ester.

The invention claimed is:

1. A process for the preparation of mycophenolate mofetil (MMF), wherein an ester of mycophenolic acid (MPA) with a low-molecular-weight aliphatic alcohol is transesterified with N-(2-hydroxyethyl)morpholine in the presence of *Candida antarctica* lipase.

2. The process according to claim 1, wherein the low-molecular-weight aliphatic alcohol is a $C_1$-$C_4$ alkyl alcohol or a halogenated derivative thereof.

3. The process according to claim 2, wherein the $C_1$-$C_4$ alkyl alcohol or its halogenated derivative is selected from methanol, ethanol, isopropanol, 2,2,2-trifluoroethanol, 2,2,2-trichloroethanol, n-propanol and n-butanol.

4. The process according to claim 1, wherein the transesterification reaction is carried out in an aprotic polar organic solvent.

5. The process according to claim 4, wherein the aprotic polar organic solvent has a log P of less than 0.5.

6. The process according to claim 4, wherein the aprotic polar organic solvent is selected from THF and dioxan.

7. The process according to claim 6, wherein the aprotic polar solvent is THF.

8. The process according to claim 1, wherein the transesterification reaction is carried out without a surfactant.

9. The process according to claim 1, wherein the amount of the lipase is from 50 to 150 mg per mmole of substrate.

10. The process according to claim 9 wherein the amount of lipase is 107 mg per mmole of substrate.

11. The process according to claim 1, wherein the concentration of the substrate is from 0.1 to 0.3 molar.

12. The process according to claim 11 wherein the concentration of the substrate is 0.25 molar.

13. The process according to claim 1, wherein the molar ratio between the MPA ester and the N-(2-hydroxyethyl) morpholine is from 0.2 to 0.4.

14. The process according to claim 13, wherein the molar ratio between the MPA ester and the N-(2-hydroxyethyl) morpholine is 0.3.

15. The process according to claim 1, wherein the transesterification reaction is carried out under agitation at a temperature of from 15 to 45° C.

16. The process according to claim 15, wherein the transesterification reaction is carried out under agitation at a temperature of from 25 to 30° C.

17. The process according to claim 1, wherein the MPA esterification reaction is carried out in the presence of *Candida antarctica* lipase using the low-molecular-weight aliphatic alcohol as the solvent.

18. The process according to claim 17, wherein the amount of lipase is from 20 to 60 mg per mmole of MPA.

19. The process according to claim 18, wherein the amount of lipase is 53 mg.

20. The process according to claim 17, wherein the concentration of MPA is from 0.05 to 0.2 molar.

21. The process according to claim 20, wherein the concentration of MPA is 0.1 molar.

22. The process according to claim 17, wherein the esterification reaction is carried out under agitation at a temperature of from 15 to 45° C.

23. The process according to claim 22, wherein the esterification reaction is carried out under agitation at a temperature of 30° C.

24. The process according to claim 17, wherein the esterification reaction is carried out without a surfactant.

* * * * *

UNITED STATES PATENT AND TRADEMARK OFFICE
CERTIFICATE OF CORRECTION

| | |
|---|---|
| PATENT NO. | : 7,727,751 B2 |
| APPLICATION NO. | : 11/661913 |
| DATED | : June 1, 2010 |
| INVENTOR(S) | : Paride Grisenti et al. |

It is certified that error appears in the above-identified patent and that said Letters Patent is hereby corrected as shown below:

On the Title Page, & Col. 1 lines 1-3 Title: "METHOD FOR THE PREPARATION OF MYCOPHENOLATE MOFETIL BY ENZYME TRANESTERIFICATION"
should be
-- METHOD FOR THE PREPARATION OF MYCOPHENOLATE MOFETIL BY ENZYMATIC TRANESTERIFICATION --.

On the Title Page, Item (22), PCT Filed: "Jul. 25, 2005" should be -- Jul. 26, 2005 --.

On the Title Page, Item (30) Foreign Application Priority Data: "MI2004A1703" should be
-- MI2004A001703 --.

Signed and Sealed this
Tenth Day of May, 2011

David J. Kappos
*Director of the United States Patent and Trademark Office*